(12) United States Patent
Delgado et al.

(10) Patent No.: US 9,134,295 B1
(45) Date of Patent: Sep. 15, 2015

(54) SERIAL ARRAYS OF SUSPENDED MICROCHANNEL RESONATORS

(71) Applicant: Massachusetts Institute of Technology, Cambridge, MA (US)

(72) Inventors: Francisco Feijó Delgado, Boston, MA (US); Nathan Cermak, Cambridge, MA (US); Selim Olcum, Cambridge, MA (US); Scott Manalis, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 45 days.

(21) Appl. No.: 14/247,779

(22) Filed: Apr. 8, 2014

(51) Int. Cl.
| | | |
|---|---|---|
| *G01N 15/06* | (2006.01) | |
| *G01N 33/00* | (2006.01) | |
| *G01N 33/48* | (2006.01) | |
| *G01N 33/50* | (2006.01) | |

(52) U.S. Cl.
CPC .................................. *G01N 33/5005* (2013.01)

(58) Field of Classification Search
USPC ......... 422/50, 68.1, 81, 82.01, 502, 503, 509; 43/43, 180
See application file for complete search history.

(56) References Cited

U.S. PATENT DOCUMENTS

| | | | | |
|---|---|---|---|---|
| 8,552,299 B2* | 10/2013 | Rogers et al. | ................. | 174/254 |
| 2008/0216564 A1* | 9/2008 | Yuan et al. | ................... | 73/61.75 |
| 2014/0355381 A1* | 12/2014 | Lal et al. | ......................... | 367/87 |

OTHER PUBLICATIONS

Lee et al., Suspended microchannel resonators with piezoresistive sensors, Lab Chip, 2011, 11, 645-651, The Royal Society of Chemistry, UK.
Lee et al., High precision particle mass sensing using microchannel resonators in the second vibration mode, Review of Scientific Instruments, 2011, 82, American Institute of Physics, US.
Bryan et al., Measuring single cell mass, volume, and density with dual suspended microchannel resonators, Lab on a Chip, 2014, 569-576, 14, The Royal Society of Chemistry, UK.
Burg et al., Weighing of biomolecules, single cells and single nanoparticles in fluid, Nature, 2007, 1066-1069, 446, Nature Publishing Group, US.

* cited by examiner

*Primary Examiner* — Brian J Sines
(74) *Attorney, Agent, or Firm* — Sam Pasternack; MIT Technology Licensing Office

(57) ABSTRACT

Serial suspended microchannel resonator sensor array. The array includes a plurality of resonator cantilevers in fluid communication with one another and a plurality of delay channels in fluid communication with, and disposed between, the resonator cantilevers. An object introduced into the array will flow in one direction and be measured by each of the cantilevers in turn after a selected delay in the delay channels.

10 Claims, 1 Drawing Sheet

SERIAL ARRAYS OF SUSPENDED MICROCHANNEL RESONATORS

This invention was made with government support under Contract Number R01GM085457 awarded by the National Institutes of Health. The government has certain rights in the invention.

BACKGROUND OF THE INVENTION

This invention relates to suspended microchannel resonators and more particularly to an array of serially-arranged suspended microchannel resonators.

Suspended microchannel resonators are well-known for measuring properties such as the mass of objects that pass through the resonator. Suspended microchannel resonators are described in the references attached hereto. A suspended microchannel resonator is a fluidic device in which objects pass along a cantilever that is oscillating. As an object moves along the resonator, the resonant frequency changes, enabling the measurement of properties such as mass of the object.

Suspended microchannel resonators are often used to analyze cells. In particular, such resonators are often used to assess cellular growth rate. Prior art single suspended microchannel resonators have a limited throughput of a few cells per hour. Cell samples that are to be screened may contain up to $10^5$ cells so that a single suspended microchannel resonator would be too slow to make a practical screening device.

It is therefore an object of the invention to provide a suspended microchannel resonator system capable of a throughput of up to $10^4$ cells per hour.

SUMMARY OF THE INVENTION

The serial suspended microchannel resonator array disclosed herein includes a plurality of resonator cantilevers in fluid communication with one another. A plurality of delay channels are provided in fluid communication with, and disposed between, the resonator cantilevers. An object such as a cell introduced into the array will flow in one direction and be measured by each of the cantilevers in turn after a selected delay in the delay channels. In a preferred embodiment, the sensor array disclosed herein is disposed on a single microfluidic chip. A suitable selected delay is approximately two minutes in one embodiment of the invention disclosed herein.

In a preferred embodiment, the resonator sensors are driven by a piezoelectric shaker and each of the cantilevers has a different length to provide different resonant frequencies to prevent coupling between resonators. A suitable offset in resonant frequencies is approximately 10 kHz. It is also preferred that the cantilevers operate in the second or higher vibrational mode. In this embodiment, fluid channels within the cantilever extend only to the node of the second vibrational mode.

DESCRIPTION OF THE PREFERRED EMBODIMENT

Figure 1:
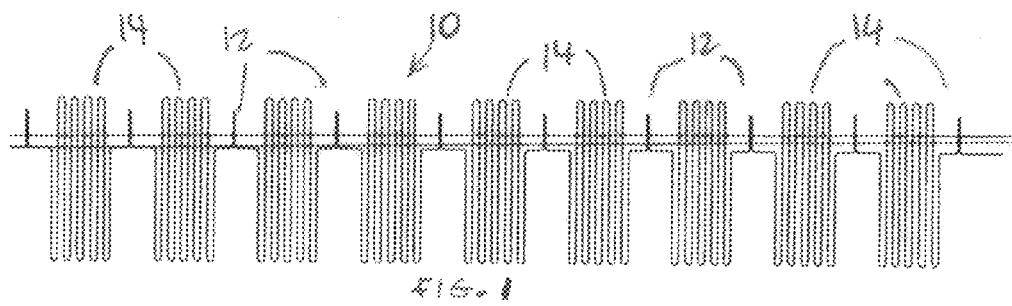
FIG. 1 is a schematic illustration of the serial suspended microchannel resonator devices along with delay channels in between each device.

With reference first to FIG. 1, a suspended microchannel array 10 includes plural cantilevers 12. The cantilevers 12 are separated by serpentine delay channels 14 disposed between each of the cantilevers 12. As shown in FIG. 1, the cantilevers are positioned along the same fluidic channel. It is preferred that the suspended microchannel resonator array 10 be placed on a single microfluidic chip. Rather than passing a single cell back and forth through a single sensor to measure growth, a cell will constantly flow in one direction and be measured by several different sensors, traversing a cantilever roughly once every two minutes. It will be appreciated that multiple cells can be measured simultaneously by the system disclosed herein since each cell only occupies a cantilever for a short time, and then spends time in the delay channel. Thus, another cell is free to pass through the suspended microchannel resonator in the meantime.

Figure 2:
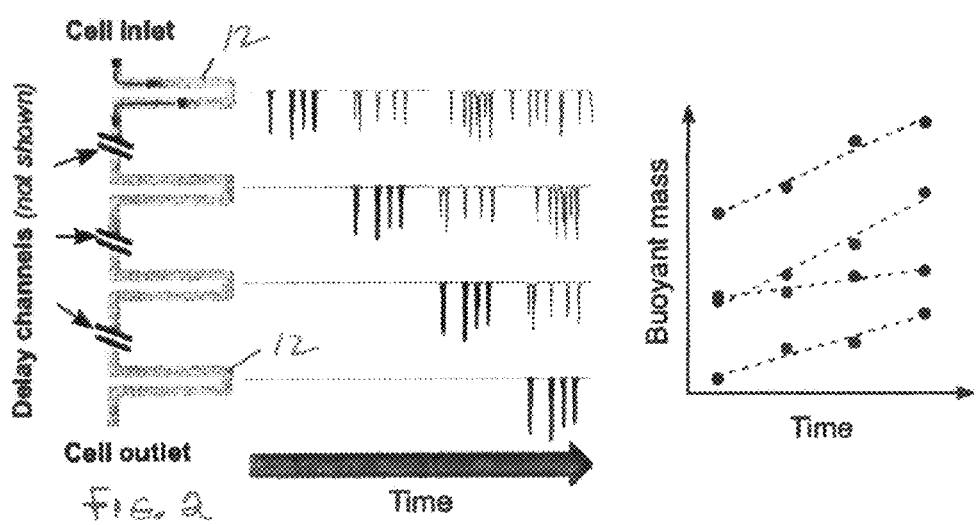
FIG. 2 is a schematic illustration of four suspended microchannel resonators along with the pattern obtained upon cell passage.

FIG. 2 illustrates the invention with a series of four cantilevers 12. In practice, it is expected that each cell will be measured approximately every two minutes over a 22 minute period and that a single array will be capable of measuring the growth rate and mass of a cell at a rate of about 400 cells per hour.

Figure 3:
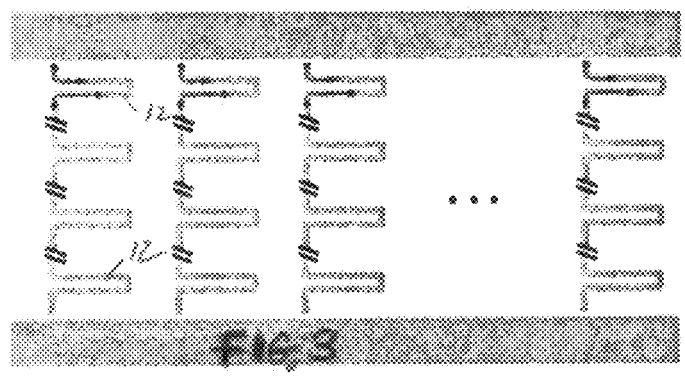
FIG. 3 is a schematic illustration of a serial suspended microchannel resonator array including 25 serial arrays, each with ten resonators.

In FIG. 3, the serial design has been parallelized to provide 25 serial arrays of ten resonators each. The design in FIG. 3 can have a throughput of up to 10,000 cells per hour.

The design of the devices disclosed herein are very similar to previous piezoresistive suspended microchannel resonator systems (1) except that there will be multiple resonators instead of only one or two. Thin piezoresistive traces are doped onto bulk silicon near the base of a resonator, where the silicon experiences maximum stress, and the resistance is read out via an on-chip Wheatstone bridge circuit, connected to an off-chip high-bandwidth, high-input-impedance difference amplifier. Although there is room for hundreds to thousands of resonators on a single 5 $cm^2$ chip, the delay channels 14 will ultimately be the limiting factor. It is estimated that about 25 serial arrays of ten resonators each with nine two-minute delay channels will be the limit for a chip of this size.

In order to run all of the suspended microchannel resonators 12 simultaneously, each resonator must be driven in positive feedback at which point it becomes an oscillator with a very high effective quality factor (on the order of $10^{10}$). However, this feedback loop relies on a method to precisely phase-shift the position signal before feeding it back to the resonator as a driving force. To keep all the resonators in feedback simultaneously, each with its own specific phase-shift, we will take the summed position signals from each resonator, use an array of digitally-implemented phase-locked loops to filter and delay the signal for a digitally-controlled time, and drive the piezoelectric shaker with this delayed signal. Note that the piezo shaker is actually driven with the sum of all the different delayed signals coming from each resonator, each with its own particular delay. The phase-locked loop operations may be performed with a field-programmable gate array (FPGA) chip using custom software.

To avoid coupling between resonators, the length of the cantilevers will be adjusted to offset their resonant frequencies by, for example, 10 kHz. The necessary bandwidth to resolve 99% of the energy in a particle signal is estimated using Carson's rule for each resonator. It is estimated that less than 2,200 Hz of bandwidth, depending on flow rate, between the cantilevers 12 will be necessary.

Figure 4:
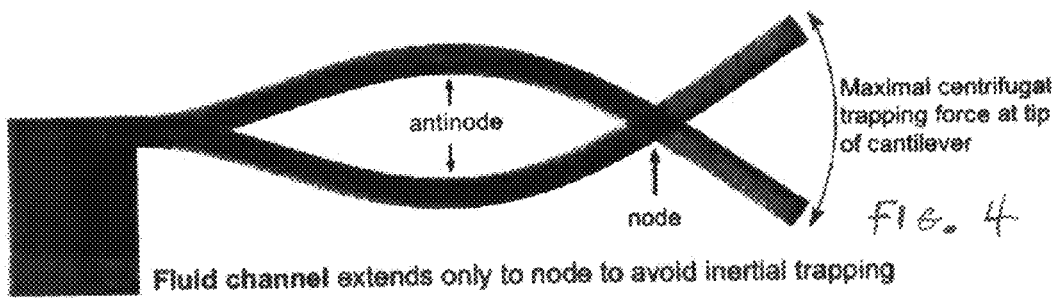
FIG. 4 is a schematic illustration of the side view of a resonator vibrating in a second mode.

The cantilevers 12 are designed to operate in the second vibrational mode where, unlike in the first mode, the signal is not affected by the particle flow path (2). However, one problem we have had with vibrating cantilevers in higher modes is that the inertial (centrifugal) force experienced by particles at the tip of the cantilever becomes substantial (due to a quadratic dependence of force on frequency), and cells are more likely to become trapped at the tips of the cantilevers. Especially at slower flow rates (less than 1 mm/sec in these flow channels), cells becoming stuck is a common problem and often requires decreasing the cantilever drive amplitude thereby increasing the noise level of the measurement. This problem is avoided by designing the cantilevers such that the internal fluidic channel extends only to the node of the second vibrational node as shown in FIG. 4. Thus, cells will never be subjected to the inertial forces that trap them at the end of the cantilever. Importantly, the high-resolution mass measurements acquired when cells pass through the antinodes will not be degraded.

The delay channels 14 are effectively parameterized by only the length and cross section. Assuming we know the time delay desired between two cantilevers $\Delta t$ and the target time for a cell to pass through a single cantilever $t_{measure}$, then the necessary volume of the delay channel is determined. For an exemplary two-minute delay between cantilevers and a single cantilever measurement time of one second, the delay channel must have a volume 120 times the cantilever volume. Therefore, if one chooses the cross section dimensions, one can calculate the necessary length. The choice of cross section geometry depends on two opposing concerns. The first is that a larger cross section exacerbates problems of unequal flow rates between different cells and potentially could result in cells passing each other and changing the arrival order of cells at different cantilevers. However, a counterargument against small cross sections is that smaller cross sections increase the possibility of clogging and increase the fluidic resistance of the channel. As a result of the high resistance, generating high flow rates to blast out clogs becomes difficult without resorting to such high pressures that might damage the microfluidic chip itself. A suitable design for the delay channels for mammalian cells has a cross section of 19 µm by 30 µm as a compromise between these two competing concerns.

As noted above, there may be a loss of ordering in the delay channels when cells are flowing at different velocities because the flow's profile is parabolic. A first solution to the problem is to decrease cell concentration such that the spacing between cells is larger. Throughput, however, will be lower. A second solution is to infer when the ordering has changed and still assign peaks to the correct cells. Because cells vary widely in their masses and grow slowly, one can cast the problem as an "assignment problem" in which one seeks to match peaks at sequential cantilevers, using the assumption that cells do not abruptly change masses, and use well-known algorithms and (Hungarian algorithms, Needleman-Wunsch) to find an optimal assignment. Such algorithms have been used previously for serial operation of dual suspended microchannel resonators (3).

The serial microchannel resonator arrays disclosed herein may be fabricated by using an established process developed for fabricating piezoresistive suspended microchannel resonators (1,4). Briefly, wafer bonding of silicon to silicon and silicon to Pyrex will be used to create free-standing vacuum packaged silicon microchannels. Devices are vacuum sealed at sub millitorr pressure and an on-chip getter will be used to insure stability of the low pressure microenvironment over extended time periods. Bypass channels for fluid delivery will be etched 30 µm deep into Pyrex wafers which will be ultrasonically drilled and anodically bonded to the silicon wafer. Fluidic interconnects to the chip are made by a Teflon manifold and perfluoroelastomer o-rings. Importantly, the fluid path contacts only silicon and Pyrex which are inert to most reagents.

The numbers in parentheses refer to the references listed herewith. The contents of all of these references are incorporated herein by reference. It is recognized that modifications and variations of the invention will be apparent to those of ordinary skill in the art, and it is intended that all such modifications and variations be included within the scope of the appended claims.

REFERENCES

1. Lee J, Chunara R, Shen W, Payer K, Babcock K, Burg T P, Manalis S R. (2011). Suspended microchannel resonators with piezoresistive sensors. Lab on a Chip, 11(4): 645-51.
2. Lee J, Bryan A K, Manalis S R. (2011). High precision particle mass sensing using microchannel resonators in the second vibration mode. Review of Scientific Instruments, 82(2).
3. Bryan A K, Hecht V C, Shen W, Payer K, Grover W H, Manalis S R. (2014). Measuring single cell mass, volume, and density with dual suspended microchannel resonators. Lab on a Chip, 14(3): 569-76.
4. Burg T P, Godin M, Knudsen S M, Shen W, Carlson G, Foster J S, Babcock K, Manalis S R. (2007). Weighing of biomolecules, single cells and single nanoparticles in fluid. Nature, 446(7139): 1066-9.

What is claimed is:

1. Serial suspended microchannel resonator sensor array comprising:
   a plurality of resonator cantilevers in fluid communication with one another; and
   a plurality of delay channels in fluid communication with, and disposed between, the resonator cantilevers;
   wherein an object introduced into the array will flow in one direction and be measured by each of the cantilevers in turn after a selected delay in the delay channels.

2. The array of claim 1 wherein the sensor array is disposed on a single microfluidic chip.

3. The array of claim 1 further including a piezoresistive readout of a measured object.

4. The array of claim 1 wherein the resonator sensors are driven by a piezoelectric shaker.

5. The array of claim 1 wherein each cantilever has a different length to provide different resonant frequencies to prevent coupling between resonators.

6. The array of claim 5 wherein the different resonate frequencies are offset by approximately 10 kHz.

7. The array of claim 1 wherein the cantilevers operate in the second or higher vibrational mode.

8. The array of claim 7 wherein fluid channels within the cantilever extend only to the node of the second vibrational mode.

9. The array of claim 1 wherein the selected delay in the delay channels is determined by volume of the delay channels.

10. The array of claim 1 wherein the object is a cell.

* * * * *